United States Patent [19]

Martini

[11] 4,118,398

[45] Oct. 3, 1978

[54] PERFLUORINATED ETHERS

[75] Inventor: Thomas Martini, Neuenhain, Taunus, Fed. Rep. of Germany

[73] Assignee: Hoechst Aktiengesellschaft, Frankfurt am Main, Fed. Rep. of Germany

[21] Appl. No.: 791,997

[22] Filed: Apr. 28, 1977

Related U.S. Application Data

[62] Division of Ser. No. 704,689, Jul. 12, 1976, Pat. No. 4,052,277.

[30] Foreign Application Priority Data

Jul. 15, 1975 [DE] Fed. Rep. of Germany ....... 2531511

[51] Int. Cl.² ........................................... C07D 319/10
[52] U.S. Cl. ........................... 260/340.6; 260/615 BF
[58] Field of Search ....................................... 260/340.6

[56] References Cited

U.S. PATENT DOCUMENTS

| | | | |
|---|---|---|---|
| 4,033,984 | 7/1977 | Martini | 260/340.6 |
| 4,035,388 | 7/1977 | Martini | 260/340.6 |

*Primary Examiner*—Ethel G. Love
*Attorney, Agent, or Firm*—Curtis, Morris & Safford

[57] ABSTRACT

Perfluorinated ethers obtainable exposing perfluorocarbonyl compounds of the formula

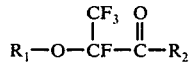

wherein $R_1$ and $R_2$ mean identical or different perfluoroalkyl radicals optionally containing one or several ether-like bound oxygen atoms to light rays having a wave length of from 100 to 600 m $\mu$, in a liquid phase.

2 Claims, No Drawings

PERFLUORINATED ETHERS

This is a division of application Ser. No. 704,689, filed July 12, 1976, now U.S. Pat. No. 4,052,277.

Thermally stable and chemically inert perfluorinated polyethers may be obtained by polymerization of tetrafluoroethylene epoxide or hexafluoropropene oxide (for example according to U.S. Pat. Nos. 3,250,808 and 3,125,599) and by subsequent stabilization of the acid fluoride terminal groups formed in the polymerization.

The acid fluoride terminal groups have already been removed catalytically in the presence of aluminum fluoride by decarbonylation at a temperature in the range of from 225° to 500° C. Under these conditions a cleavage of the molecule may however occur (Cf. U.S. Pat. No. 3,018,306). In the pyrolysis of the alkali metal salts of the acid corresponding to the acid fluoride (according to U.S. Pat. No. 2,668,864) there are only obtained perfluorinated vinyl ethers having an unsufficient thermal and chemical stability. It is moreover possible to stabilize the acid fluoride terminal groups directly (Cf. German Offenlegungsschrift No. 1,770,126) or after conversion of the acid fluoride into the free carboxylic acid (Cf. U.S. Pat. No. 3,242,218) by means of fluorine with splitting off of $COF_2$ or $CO_2$. This procedure has the disadvantage that the process may only be performed with considerable expenditure and great precaution, as elementary fluorine is used. Acid fluorides react under exposure to light while splitting off $COF_2$ and CO. Simultaneously there are formed "dimeric" perfluorinated ethers. This reaction however takes place partially with low yields and requires very long times of exposure.

The present invention seeks to provide a process permitting preparation of perfluorinated ethers free from carbonyl groups with high yields without using elementary fluorine.

The object of the present invention consequently is a process for preparing perfluorinated ethers, which comprises exposing perfluorocarbonyl compounds of the formula II

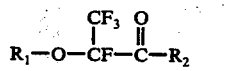

wherein $R_1$ and $R_2$ represent identical or different perfluoroalkyl radicals optionally containing one or several oxygen atoms in etherlike linkage, in a liquid phase, to light rays having a wave length of from 180 to 600 m μ.

In principle the process may be applied to all compounds of the formula II. Especially good yields are obtained when $R_1$ and $R_2$ have a total of at least 10, preferably at least 14 carbon atoms. Acceptable yields are still obtained when $R_1$ and $R_2$ have together at most 80, preferably at most 60 carbon atoms. According to a preferred process there are used symmetrical ketones, i.e. ketones wherein $R_2$ is $R_1$—O—CF($CF_3$)—.

The reaction may be represented by the following equation:

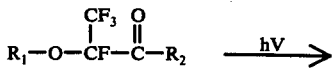

II

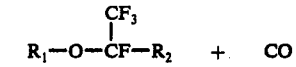

I

The compounds of the formula II may be obtained by reaction of perfluorovinyl ethers of the formula $R_1$—O—CF=$CF_2$ with perfluorinated acid fluorides of the formula $R_2$—COF in an aprotic polar solvent in the presence of cesium fluoride at a temperature of from −20° to +180° C according to German Pat. No. P 25 21 594.5.

The radicals $R_1$ and $R_2$ in this process for preparing the perfluorinated ketones each may have especially from 6 to 30, preferably from 10 to 25 carbon atoms. They may be linear, branched or cyclic.

Examples of oxygen-containing radicals $R_1$ are especially perfluoro-2-propoxy-propyl, perfluoro-2,5-dimethyl-3,6-dioxanonyl, and perfluoro-2,5,8,trimethyl-3,6,9-trioxadodecyl.

Among suitable oxygen-containing radicals $R_2$ there may be mentioned especially perfluoro-2-propoxy-ethyl, perfluoro-1,4-dimethyl-2,5-dioxaoctyl, and perfluoro-1,4,7-trimethyl-2,5,8-trioxaundecyl.

The number of the oxygen atoms in ether-like linkage optionally contained in the radicals $R_1$ and $R_2$ may amount to up to half the number of the carbon atoms of the radicals $R_1$ or $R_2$ (when calculated on the polymer of perfluoroethylene epoxide) or up to about a third of the number of the carbon atoms of the radicals $R_1$ or $R_2$ (when calculated on the polymer of perfluoropropylene oxide).

The following vinyl ethers and acid fluorides formally derived from dioxane may be mentioned among suitable cyclic starting compounds having several oxygen atoms in ether-like linkage:

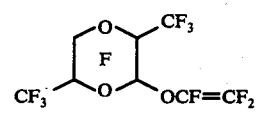

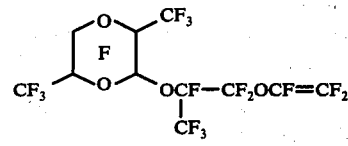

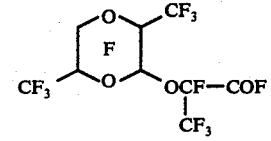

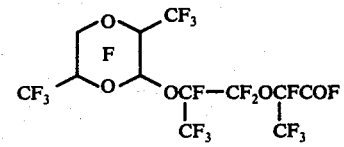

The formula

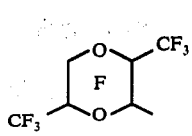

is a simplified form of the formula

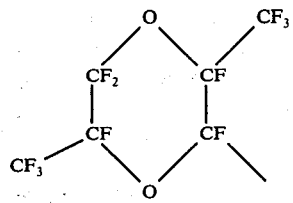

Under the action of light CO is split off from the compounds of the formula II, which compounds are converted thereby into compounds of the formula I. As a source of radiation there are preferably used inter alia mercury high-pressure lamps, the spectral energy distribution of which has maximum values in the range of from 366 to 540 m μ.

It is preferably operated in the following manner: The lamp covered with a quartz tube is either directly immersed into the liquid to be exposed and the heat produced by the lamp is dissipated by cooling or the lamp is provided with a cooling jacket of quartz glass. As cooling medium there may be used, for example the air or $N_2$.

The exposure to light is preferably performed in an inert gas atmosphere, by introduction of a $N_2$ current through a frit at the bottom of the exposure vessel. Thus mixing is assured at the same time.

The reaction temperature may be in the range of from −40° to +200° C, preferably of from 0° to 150° C. Higher temperatures do not bring about any advantage, but may even produce secondary reactions.

The end of the reaction may be easily observed by the disappearance of the CO absorption band in the infra-red spectrum at about 5.6 μ characteristic for the carbonyl compound.

The product obtained is colorless and transparent. The reaction takes place practically quantitatively.

When the viscosity of the material to be exposed to light is too high the reaction may also be performed in an inert solvent. Examples thereof are carbon fluorides such as perfluorohexanes or perfluorononanes as obtained for example by fluorination of dimeric and trimeric compounds of hexafluoropropene.

P. B. Ayscough and W. R. Steacie describe the photolytic cleavage of CO from hexafluoroacetone with the formation of hexafluoroethane by photolysis in the gaseous phase under a pressure below 100 mm Hg in Proc. Roy. Soc. (London) 234, 476 (1956). The quantum yield however is vigorously reduced in the cited process with an increasing pressure-especially at a temperature of 100° C, as the excess of oscillation energy is lost by collisions with adjacent molecules. [Cf. G. B. Porter, Angew. Chemie 75, 422 (1963)].

The compounds prepared according to the present invention are valuable products which may be used in a wide field of application owing to their chemical and thermal stability, for example as lubricating agents cooling agents, heat transferring agents or dielectric agents. The process has the advantage that it permits obtaining a homogeneous final product from homogeneous starting compounds even of high molecular weight, the molecular weight of which final product is only reduced by 28 (CO). In the known polymerization of hexafluoropropene epoxide or tetrafluoroethylene epoxide there is always obtained a number of products having a different degree of polymerization. This homogeneity will be desirable in most cases, for example when using heat transferring agents for soldering processes. This process designated as "Condensation Soldering" has been published in 1974 (Cf. R. C. Pfahl, J. C. Mollendorf, T. Y. Chu, Nepcon WEST 1974).

The following examples illustrate the invention:

EXAMPLE 1

Perfluoro-(5,8,11,12,15,18-hexamethyl-4,7,10,13,16,19-hexaoxaheptacosane

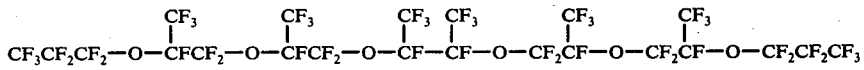

A mercury high-pressure lamp of the type Original Hanau Q 81 provided with a cooling jacket was introduced into a quartz vessel of a length of 27 cm and a diameter of 5 cm, provided with a frit at the bottom and a mounted condenser and the vessel was fed with 533 g of perfluoro-di-(1,4,7-trimethyl-2,5,8-trioxaundecane)-ketone of the formula

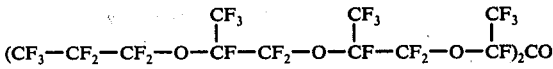

(Sdp. 100° C/0,5 Torr)

A slight $N_2$ current was introduced by the frit and the lamp was cooled by a vigorous nitrogen current. The vessel was immersed into a cold bath consisting of methylene chloride and dry-ice for external cooling and the content of the vessel was exposed to light for 14 hours at 20° C. 514 g of the product were obtained (boiling point of from 271° to 273° C). The infra-red and the mass spectrum and the analysis confirmed the structure.

EXAMPLE 2

Perfluoro-2,3-bis-(3',6'-dimethyl-1',4'-dioxane-2'-oxy)-butane

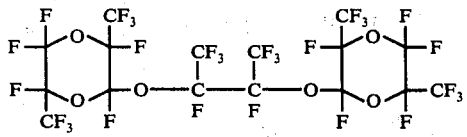

An apparatus as described under 1 was filled with 500 g of perfluoro-2,4-bis-(3',6'-dimethyl-1',4'-dioxane-2'-oxy)-pentanone-3 having the formula

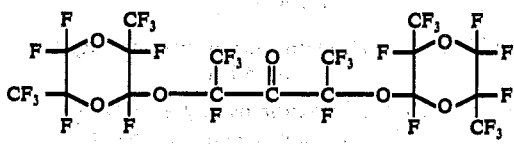

(boiling point of from 219° to 221° C) and the contents were exposed to light as in Example 1. After a time of exposure of 19 hours at 20° C the CO absorption band had disappeared in the infra-red spectrum. 458 g of product were obtained having a boiling point of from 215,5° to 220° C. Infra-red and mass spectra and the analysis confirmed the structure indicated above.

EXAMPLE 3

Perfluoro-5,8,9,12-tetramethyl-4,7,10,13-tetraoxahexadecane $$CF_3-CF_2-CF_2-O-\underset{\underset{CF_3}{|}}{CF}-CF_2-O-\underset{\underset{CF_3}{|}}{CF}-\underset{\underset{CF_3}{|}}{CF}-O-CF_2-\underset{\underset{CF_3}{|}}{CF}-O-CF_2-\underset{\underset{CF_3}{|}}{CF_2}$$

As indicated in Example 1 424 g of perfluoro-di-(5-methyl-3,6-dioxanonyl)-ketone of the formula

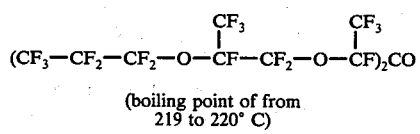

(boiling point of from 219 to 220° C)

were exposed to light for 16 hours at 20° C. 398 g of hexadecane were obtained having a boiling point of from 210° to 215° C.

The infra-red and masse spectra and the analysis indicated that the carbonyl groups had been split off quantitatively.

EXAMPLE 4

234 g of a mixture of perfluorinated polyether ketones having a boiling point of from 130° to 270° C under a pressure of from 0.3 to 0.5 torr, which had been prepared by reaction of a polymer of hexafluoropropene epoxide having a terminal vinyl ether group (boiling point of from 123° to 170° C under a pressure of from 0.3 to 0.1 torr) with a polymer of hexafluoropropene epoxide having a terminal acid fluoride group (boiling point of from 93° to 195° C/0.1 torr) in diglyme and in the presence of CsF, were exposed at a temperature of from 130° to 150° C by means of a mercury high-pressure lamp, whereby the lamp was not cooled. After disappearance of the carbonyl band the reaction product was distilled to yield 220 g of a perfluorinated polyether having a boiling point in the range of from 100° to 300° C/0.5 torr.

EXAMPLE 5

318 g of perfluoro-di-(5-methyl-3,6-dioxanonyl-2-)ketone were exposed to light at a temperature of from 160° to 170° C as described in Example 1. The temperature was attained owing to the heat of the lamp, the characteristic CO absorption band had completely disappeared after 10 hours.

EXAMPLE 6

Perfluoro-2,9-bis-(3',6'-dimethyl-1',4'-dioxane-2'-yloxy-)-5,6-dimethyl-4,7-dioxa-decane Perfluoro-[di-(1,4-dimethyl-2,5-dioxa-5-(3',6'-dimethyl-1',4'-dioxane-2'-yl)]-ketone were exposed to light in an analogous manner to Example 2. A product of the formula

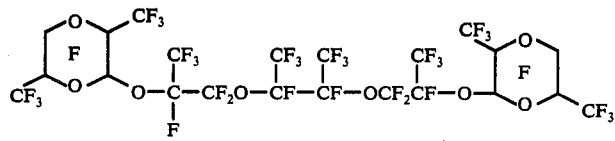

was obtained having a boiling point in the range of from 270° to 275° C. The structure could be confirmed by infra-red and mass spectra and by CF analysis.

EXAMPLE 7

Perfluoro-2,4-bis-(3',6'-dimethyl-1,4-dioxane-2-oxy)-pentanone-3

100 ml of diglyme and 40 g of CsF were introduced into a three-necked flask provided with a reflux condenser, a stirrer and a thermometer and 476 g (1.0 mol) of perfluoro-[α-(3,6-dimethyl-1,4-dioxanyl-2-oxy)]-propionic acid fluoride were added thereto. The mixture was stirred for 2 hours at room temperature and 410 g (1.0 mol) of perfluoro-3,6-dimethyl-1.4-dioxanyl-2-vinyl ether were slowly added in a liquid phase. The mixture was thereafter stirred for 1 week at 30° C, both phases were separated from one another and the lower phase was distilled, 690 g (78.8% of the theory) of the compound

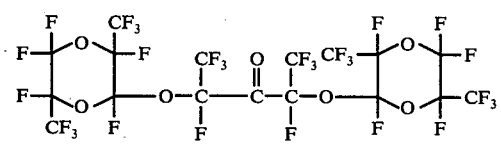

$C_{17}F_{30}O_7$ molecular weight 886, were obtained, having a boiling point of from 219° to 221° C.

Analysis: calculated: C, 23.0%; F, 64.3%. found: C, 22.9%; F, 63.6%.

The structure could be confirmed by IR, NMR and mass spectra.

EXAMPLE 8

Perfluoro-3,6-dimethyl-1,4-dioxanyl-2-vinyl-ether 2800 g of a mixture of hexafluoropropene epoxide and hexafluoropropene (in a weight ratio of 65:35) were introduced into a solution of 600 ml of diethylene glycol dimethyl ether and 600 g of PO[N(CH$_3$)$_2$]$_3$ in a three-necked flask provided with an intensive condenser, a stirrer and a thermometer for low temperatures, at a temperature from −40° to −30° C while continuously stirring, at a rate of 40 l/h (measured under normal conditions of temperature and pressure, i.e. at 0° C and under 760 mmHg).

Thereafter the reaction mixture was stirred for 5 hours at the above mentioned temperature. By slowly heating to 0° C hexafluoropropene and the excess of epoxide were expelled and the two phase mixture was separated in the separation funnel. The lower phase (1742 g) was washed with 600 ml of acrylonitrile and yielded 1554 g of product mixture, from which 1142 g of a substance boiling at a temperature from 115° to 118° C and 194 g of a second fraction boiling at a temperature from 118° to 170° C could be obtained by fractionated distillation, the first one having the formula

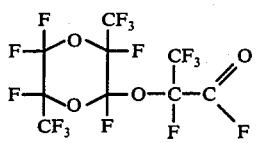

according to elementary, IR and NMR-spectroscopic analyses and representing the hitherto unknown perfluoro-[α-3,6-dimethyl-1,4-dioxanyl-2-oxy]-propionic acid fluoride.

794 g (1.67 mol) of this substance were added dropwise to 160 ml of water while cooling with ice and stirring. The mixture obtained was then neutralized with 20% KOH solution and concentrated at the rotation evaporator. The material thus predried was kept on a sheet in a vacuum drying oven for 24 hours at 100° C under 300 torrs, ground to fine particles and again heated for the same period to 100° C under 0.1 torr.

The dry product obtained was heated for 30 hours to a temperature from 200° to 225° C in a vacuum of from 5 to 0.1 torr in a 2 liter round-bottomed flask being connected with two following cold traps. The collected pyrolysate (628 g) was distilled by fractionation.

After a first fraction of 8 g (boiling point from 97° to 103° C) there were obtained 584 g (85,2% of the theory) of perfluoro-3,6-dimethyl-1,4-dioxanyl-2-vinyl ether having a boiling point from 103° to 106° C.

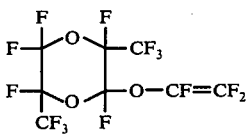

$C_8F_{14}O_3$ molecular weight 410.

Analysis: calculated: C, 23.4%; F, 64.9%. found: C, 23.6%; F, 65.2%.

IR and $^{19}$-F-NMR spectra confirmed the structure. A strong band appeared at 9.65 μ in the IR spectrum.

Distilling residue: 32 g.

EXAMPLE 9

Perfluoro-[α-(3,6-dimethyl-1,4-dioxanyl-2-oxy-propyl)-vinyl ether]

From the second fraction having a boiling point from 118° to 170° C which had been obtained in the preparation of perfluoro-[α-(3,6-dimethyl-1,4-dioxanyl-2-oxy)]-propionic acid fluoride according to Example 1 there were obtained 67% by weight of a compound having a boiling point in the range from 160° to 164° C by a further fractionated distillation, which compound corresponded to the formula

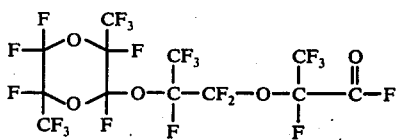

$C_{12}F_{22}O_5$ molecular weight 642, according to the elementary, IR and NMR-spectroscopic analyses and represented the hitherto unknown perfluoro-[α-(3,6-dimethyl-1,4-dioxanyl-2-oxypropoxy)]-propionic acid fluoride.

Analysis: calculated: C, 22.4%; F, 65.2%. found: C, 22.3%; F, 65.0%.

623 g (097 mol) of this acid fluoride were introduced dropwise into 100 ml of water while cooling with ice. The reaction mixture was then neutralized with 10% KOH and concentrated at the rotation evaporator. The predried material was then kept for 15 hours at a temperature of 100° C/300 torrs and dried thereafter for 62 hours at a temperature of 100° C/0.1 torr. Then it was heated to 200° C under a pressure from 5 to 0.1 torrs for 24 hours.

By distilling the pyrolysate obtained in analogous manner to Example 1 346 g (61.9% of the theory) of a vinyl ether were obtained having a boiling point from 151° to 154° C and corresponding to the structure

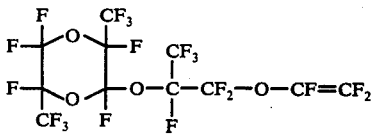

$C_{11}F_{20}O_4$ molecular weight 576.

Analysis: calculated: C, 22.9%; F, 65.9%. found: C, 22.8%; F, 65.6%,
according to the NMR, IR and mass spectrometry as well as to the elementary analysis.

What is claimed is:

1. The compound perfluoro-2,3-bis-(3',6'-dimethyl-1',4'-dioxane-2'-yloxy)-butane.

2. The compound perfluoro-2,9-bis-(3',6'-dimethyl-1',4'-dioxane-2-yl-oxy)-5,6-dimethyl-4,7-dioxadecane.

* * * * *